United States Patent [19]

Stapleton

[11] Patent Number: 5,436,129
[45] Date of Patent: Jul. 25, 1995

[54] PROCESS FOR SPECIMEN HANDLING FOR ANALYSIS OF NUCLEIC ACIDS

[75] Inventor: Marilyn J. Stapleton, Durham, N.C.

[73] Assignee: Gene Tec Corp., Durham, N.C.

[21] Appl. No.: 135,131

[22] Filed: Oct. 12, 1993

Related U.S. Application Data

[60] Continuation of Ser. No. 929,720, Aug. 12, 1992, abandoned, which is a division of Ser. No. 438,592, Nov. 17, 1989, Pat. No. 5,188,963.

[51] Int. Cl.$^6$ .............. C12Q 1/68; C12P 19/34; C25B 1/00; B01D 61/42

[52] U.S. Cl. ................ 435/6; 435/91.1; 435/91.2; 435/287; 435/299; 436/177; 436/178; 436/515; 436/516; 422/56; 422/58; 422/61; 422/69; 422/101; 422/102; 422/104; 204/182.6; 204/182.8; 204/182.9; 204/299 R; 935/76; 935/77

[58] Field of Search ............... 435/6, 91.1, 91.2, 287, 435/299; 436/807, 820, 177, 178, 515, 516; 422/56, 58, 61, 69, 101, 102, 104; 204/182.6, 182.8, 182.9, 299 R; 935/76, 77

[56] References Cited

U.S. PATENT DOCUMENTS

| | | | |
|---|---|---|---|
| 4,683,195 | 7/1987 | Mullis | 435/6 |
| 5,021,335 | 6/1991 | Tecott et al. | 435/6 |
| 5,024,934 | 6/1991 | Lee | 435/6 |

OTHER PUBLICATIONS

Hurley et al., *Biopolymers*, vol. 25, pp. 539–554, issued 1986.
Tecott et al., *Science*, vol. 240, pp. 1661–1664, issued 17 Jun. 1988.
*Nucleic Acids Research*, Sommer and Tautz, "Minimal homology requirements for PCR", vol. 17, No. 16, 1989, p. 6749.

*Primary Examiner*—Margaret Parr
*Assistant Examiner*—Bradley L. Sisson
*Attorney, Agent, or Firm*—Olive & Olive

[57] ABSTRACT

A process for handling a biological specimen for the analysis of nucleic acid sequences wherein the biological specimen is immobilized within a carrier device for controlled temperature conditions and the sequential addition of fluid treatments. The fluid treatments arm selected from lysing end denaturing solutions, wash or rinse solutions, reagents for nucleic acid amplification, electrophoresis and hybridization and labeling and detection reagents. The fluid treatments are unique to each specimen and the detection of target nucleic acid sequences is localized within the carrier device.

5 Claims, 3 Drawing Sheets

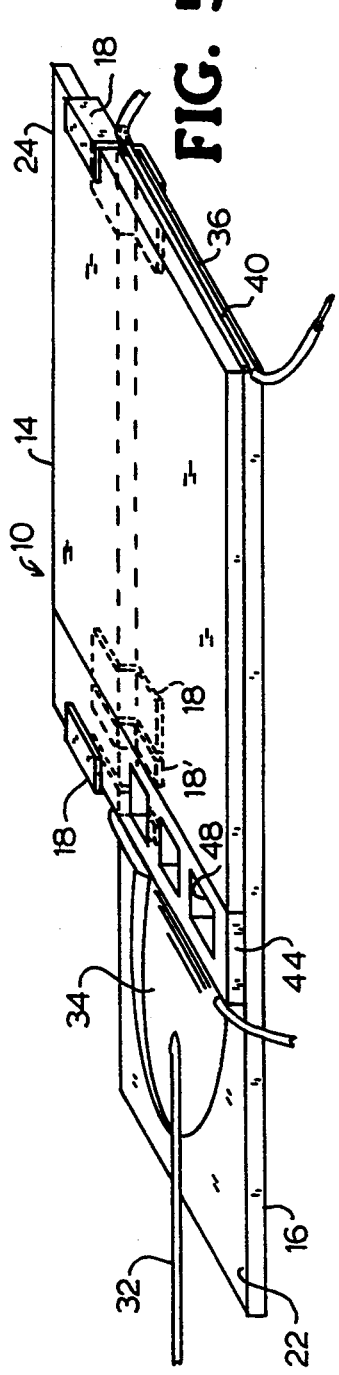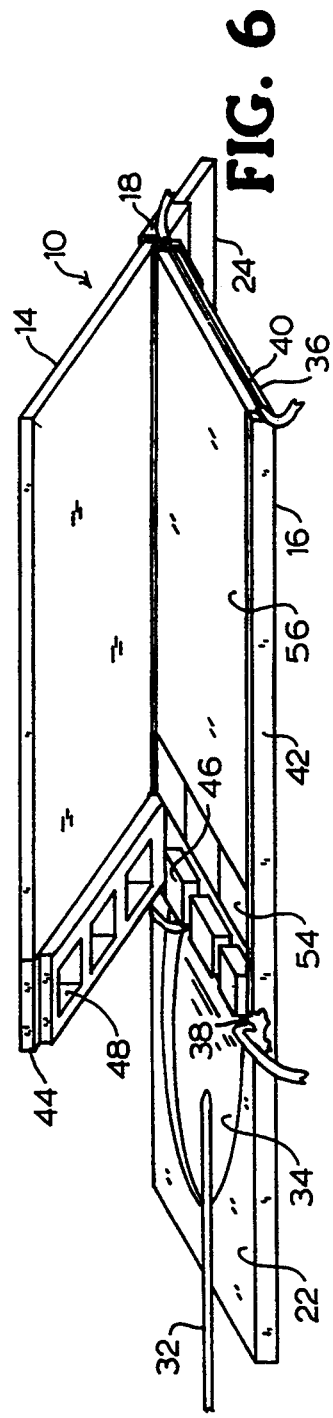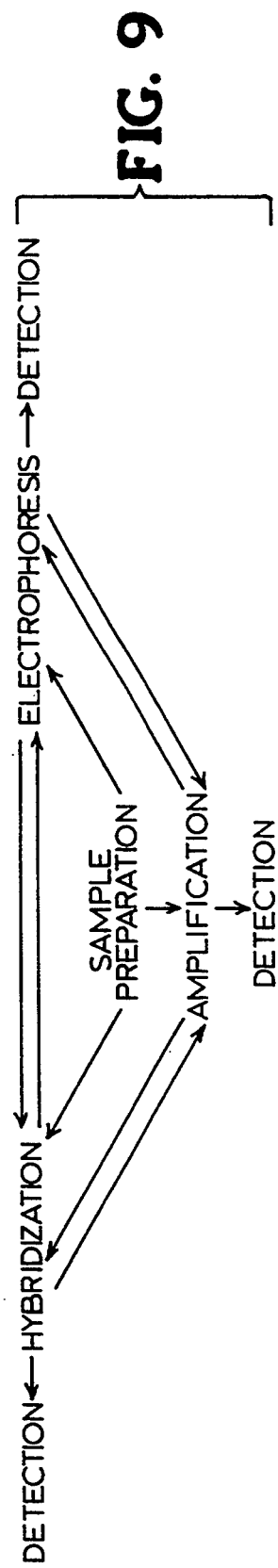

PROCESS FOR SPECIMEN HANDLING FOR ANALYSIS OF NUCLEIC ACIDS

CROSS REFERENCE TO RELATED APPLICATIONS

This is a continuation of application Ser. No. 07/671,204 filed Mar. 18, 1991.

This patent application is a continuation of application Ser. No. 07/929,720, filed Aug. 12, 1992, abandoned, which is a divisional of application Ser. No. 07/438,592 filed Nov. 17, 1989, U.S. Pat. No. 5,188,963.

BACKGROUND OF THE INVENTION

1. Field of the Invention

This invention relates to a device for use in automating the detection of target nucleic acid sequences in biological-containing samples. The device described herein is for use with an automated process, including a fluid-delivery system and a thermal reaction chamber, as is described in U.S. patent application Ser. No. 07/227,348, filed Aug. 2, 1988 and now abandoned in favor of a continuing application Ser. No. 07/935,637, filed Aug. 24, 1992. The disclosure of the co-pending application is hereby incorporated herein by reference.

The invention in said co-pending application relates to a method and apparatus for automating the detection of target nucleic acid sequences in biological-containing samples involving a sequence of physical and chemical reactions, and more particularly to a system for the exposure of, amplification of, and labelled-probe coupling to, a specific, known nucleic acid sequence. The invention is especially suited to the automated detection of single, specific genetic sequences present at random in multiple samples containing biological material without labor-intensive DNA extraction and purification procedures being performed separately on each sample.

2. Description of the Related Art

Devices for receiving biological specimens for diagnostic purposes are varied and adapted to the methods of detection. The devices may take the form of tubes for liquid specimens, flat surfaces such as glass slides suitable for microscopy, microtiter dishes, Petri dishes and cubes containing growth medium, or filters made of various materials to which cell and viral components will adhere.

These specimen samples are then treated in such a way as to indicate either the presence or absence, or quantity, of a specific biological entity. Test reagents may either be preapplied to the device or added in series after the specimen is present. Test results are read manually by a technical person or automatically with instrumentation specifically designed for that assay. In some instances the specimen is diluted with a diluent, or an aliquot of the specimen is removed from the original collecting device and transferred to another vessel at some point in the assay. In some cases physical and chemical means are used to amplify the signal of the assay for greater sensitivity. Some assays require extraction or separation to isolate a specific component from other parts.

In DNA-based diagnostics the sequence specificity of base-pairing or enzymatic or other types of cleavage is exploited. The linear sequence of nucleotides in double-stranded DNA molecules forms the basis of replication of the genetic code. Hybridization is the binding of two single-stranded DNA strands whose base-pairing sequences are complementary. Temperature and salt concentration affect the stringency of these base-pairing matches. A change from high stringency to low stringency can cause the same DNA probe to be either exquisitely specific to detect a particular target or less specific and detect a group of related targets.

Wherever a unique, organism-specific polynucleotide sequence is identified, it is possible to use a labeled, synthetic molecule of the unique sequence to determine the presence of the organism by hybridization of the unknown sample to the labeled sequence. This detection method involves hybridization between DNA:RNA hybrids or DNA:DNA duplexes. The probe is a single-stranded nucleic acid molecule complementary to a unique nucleic acid sequence of the gene being tracked. The probe is labeled with an identifying molecule and introduced to the test sample. Hybridization has been an important research tool, but its use is limited to a few clinical laboratories because of the time, skill and knowledge required of the technician performing the test. DNA probes are being used as commercial diagnostics for a few infectious or genetic diseases, but their individual cost is prohibitive for mass screening.

While the common laboratory procedure for hybridization binds the target DNA to a solid support, an alternative approach is solution hybridization or hybridization which requires individual column separation of the unbound, labeled probe for each sample. This invention uses a gel matrix as a solid support. It is not necessary to transfer DNA to a membrane filter after purification and amplification. This approach eliminates any loss of DNA that occurs during transfer. (Purrello and Balazs, 1983, *Anal. Biochem.* 128:393–397).

Presently DNA preparation and amplification require labor-intensive protocols just as hybridization methods do. The only apparatus which automates DNA preparation is the Applied Biosystems Nucleic Acid Extractor, which will process sixteen tissue samples simultaneously in four hours. The sample must comprise homogenous tissue and already contain enough copies of the target DNA to be detected, i.e. about a million copies. The laboratory technician must then either fractionate the extracted DNA by gel electrophoresis or transfer the DNA to a solid support for detection by hybridization to a labeled probe. There is no laboratory apparatus or equipment currently on the market that automates hybridization so that it may be left unattended.

Suspending cells in agarose beads or cubes is a common laboratory procedure for preparing unsheared nucleic acid molecules for subsequent enzymatic modifications. (P. R. Cook, 1984, *EMBO* 3:1837–1842 and L. Van der Ploeg et al. 1984. *Cell:* 37:77–84). After solidification the agarose beads or cubes are subjected to extensive treatment with detergent, protease and salt. It is possible to remove all cellular constituents except DNA because the pores in the agarose matrix are large enough to allow rapid diffusion of proteins and other small macromolecules while quantitatively retaining genomic DNA (Smith and Cantor, 1986, Cold Spring Harbor Symposium on Qualitative Biology 51:115–122).

FMC Bioproducts, Rockland, Me., has a nonradioactive-label for DNA in which their product information states that the labeling is done directly in diluted, remelted agarose. This protocol allows electrophoretic fractionation of DNA in agarose and then quick and easy preparation of specific probes (Resolutions 1987 Newsletter 3(2):1–2). FMC also markets a new grade of agarose certified for reliable restriction endonuclease activity. Many other examples exist where research scientists are performing enzymatic modifications on DNA in agarose. D. Persons and O. Finn, (Biotechniques, 1986, 4:398–403) reported primer extension of cDNA on a poly A+ RNA template using a reverse transcriptase in remelted agarose. The method and device of this invention also involves primer extension with polymerase enzymes in agarose.

Immunodiagnostics are commonly used to identify organisms directly by antigenic determinants or to identify individuals by their antibodies which are produced by exposure to the antigen. The same problem is encountered with antigen identification as with DNA probes, i. e. the organism must be cultured if it is not present in sufficient numbers for detection. There is no in vitro method to amplify antibody- binding antigens accurately like there is with primer extension gene amplification. Low population targets in a mixed background cannot be identified immunologically. The gene amplification in vitro has given DNA probes the potential to outperform immunological detection. The accuracy, sensitivity and quantitation potential of DNA probes will make them the diagnostic of choice.

An automated system for simultaneously detecting target nucleic acid sequences from multiple samples must accommodate several different steps and varying reaction conditions. It must be constructed to change reagents and solvents automatically for each stage and monitor time, temperature and pH. If tests are automated and the same apparatus that performs one test for multiple samples in one run could be used for many different tests by changing a few selected reagents, the cost of gene detection would be relatively inexpensive and the system would supersede other methods because of its speed and preciseness.

In order to have enough gene copies for detection, present methods rely on selective cultivation of the organism which takes days to weeks depending upon the organism. A selective DNA amplification technique has been practiced whereby synthetic primers are annealed to single stranded or denatured, double-stranded nucleic acid target sequences and polymerase molecules incorporate nucleotides that replicate a portion of the nucleic acid extending from the primers. Using excess primers in pairs bordering a target sequence in a way that each polymerase extension includes sequences that are complementary to the other primer sequence is a method now termed polymerase chain reaction (PCR) (see U.S. Pat. Nos. 4,683,195 and 4,683,202). This method continues in repetitive rounds of replication until the target sequence has been amplified by a factor of more that 10 million. Saiki et al. reported that a thermostable DNA polymerase improves the specificity, yield, sensitivity and length of products that can be amplified (Saiki, R. K., D. H. Gelfand, S. Stoffel, S. J. Scharf, R. Higuchi, G. T. Horn, K. B. Mullins, and H. A. Ehrlich, Science, 1988, 239:487–491). A selective gene amplification protocol that can duplicate a single copy of a nucleic acid target in vitro to a sufficient number of copies that can be detected over non-specific background binding with a labeled hybridization probe is the level of sensitivity that will enable easy screening of multiple samples. The accuracy of a gene detection is assured by labeling a probe complementary to a polynucleotide sequence between the two primer sequences for the purpose of hybridization identification. Thus, even if the primers had amplified non-target sequences because of duplicity of sequence or mismatch, the label would only be detected that bound to the target sequence.

The ability to amplify a single target DNA and/or RNA sequence enough to detect it without the cultivation of cells or organisms will simplify gene detection and attempts to automate it. Saiki et al. reported that PCR detects a single copy of target DNA present in one in 1.5 million cells. There is no reason to doubt that gene amplification by primer extension will detect a target DNA segment present at one copy per organism in the starting material. The ability to then quantify how many original copies or organisms there were per sample before amplification will make mass sampling and fate-monitoring possible by hybridization detection. Quantifying methods depend upon diluting the amplified gene so that individual signals are enumerated or intensity of total signal matches that of a known standard concentration.

Using the aforementioned gene amplification protocol, the presence of HIV-1 in peripheral blood mononuclear cells (PBMC) was determined by in situ hybridization to DNA from the PBMC's without prior cultivation of them (Ou, C., S. Kwok, S. Mitchell, D. Mack, J. Sninsky, J. Krebs, P. Feorino, D. Warfield, and G. Schochetman, Science, 1988, 239:295–297). This direct detection method reduces the time to three days from the three to four weeks required for cell cultivation and virus isolation. The polymerase chain extension technique started with DNA isolated from PBMC's, repetitively amplified the target DNA in solution, and analyzed bands on an autoradiogram produced by gel electrophoresis of restriction enzyme digests of the target DNA bound to end-labeled radioactive probe molecules.

In some instances the sizes of DNA fragments, produced by restriction endonuclease digestion or by amplification of a target sequences between primer pairs, are used to make a DNA-print for individual identification or aid in diagnosis of a genetic disease, cancer or infectious disease. For example, electrophoresis may be used to size-fractionate different-sized nucleic acids which have been specifically cleaved or whose native length puts them in a distinguishable size-length class. In the electrophoresis method, a current is applied to DNA loaded at the cathodal end of a gel matrix, which causes the DNA to migrate towards the anodal end of the matrix. The electrophoretic mobility of DNA is dependent on fragment size and is fairly independent of base composition or sequence. Resolution of one size class from another is better than 0.5% of fragment size (Sealy P. G. and E. M. Southern. 1982. Gel electrophoresis of DNA, p. 39–76. In D. Rickwood and B. D. Hames (EDS.), Gel Electrophoresis of Nucleic Acids. IRL Press, London). This reference and all other publications or patents cited herein are hereby incorporated by reference.

Electrophoresis methods thus require a vessel to hold the matrix material and the biological specimens to be subjected to electrophoresis. Such vessels may mold the gel matrix during its formation and may hold it during processing.

Diffusion of reagents is faster where the ratio of the matrix surface area to matrix volume is greatest as in thin, flat matrices. Likewise, electrophoresis of macromolecules requires less voltage and is faster in ultra-thin matrices or tiny (glass) capillaries. In these aqueous matrices, the vessel is necessary to prevent evaporation and to add strength in handling. Existing vessels that enclose matrices impede rapid diffusion of reagents and molecular probes. Once the existing vessels are taken apart in processing, they cannot be put back together to continue automated processing.

Accordingly, the invention aims to provide a system for automated gene identification of multiple samples, which prepares nucleic acids in the samples for testing, sufficiently amplifies target nucleic acid sequences and accurately detects their presence or absence in the samples.

Accordingly, the invention aims to provide a vessel for the individual specimens to be contained.

Yet another object of the invention is to mold matrix material which is to contain the specimen.

A further object of the invention is to carry the specimen in transport from the point of collection to the processing point.

A further object of the invention is to provide support of the specimen, embedding it in a matrix for automated processing.

A further object of the invention is to provide a convenient way to make the particles containing target nucleic acids of a specimen in a matrix available for optimal signal detection.

A further object of the invention is to allow for saturating specimens quickly with a series of solutions or for drying them automatically.

A further object of the invention is to concentrate specimen nucleic acids, or amplified products thereof, for detection of their presence.

A further object of the invention is to provide such a system wherein airflow and heating regulate temperature and humidity.

A further object of the invention is provide a barrier to evaporation of solutions during processing.

A further object of the invention is a mechanism to change its configuration during processing of the specimen to adapt to processing conditions.

A further objective of the invention is to provide support for reading the test results.

A still further object of the invention is to permanently store the nucleic acids present in the specimen for possible retesting and serve as a permanent record of the test, if an archival record is desired.

Other objects and advantages of the invention will be more fully apparent from the ensuing disclosure and appended claims.

SUMMARY OF THE INVENTION

The automation of this invention makes direct detection available for innumerable clinical diagnoses and for environmental gene-tracking. Current practice for tracking microbes released into the environment is done by selecting marker genes on the same episome or genome as the engineered rDNA. The system of this invention provides direct, simultaneous monitoring of the rDNA from many samples without the time and expense required to cultivate the microbe. The frequency of the target sequence in the sample can be determined by measuring hybridization of the label to the single gene targets in situ. The target DNA in each sample is immobilized, exposed, amplified and located in a series of treatments to the matrix block in which the sample has been introduced.

The DNA present in the sample that has been introduced into an individual matrix remains anchored in the corresponding matrix and is separated from the other cellular particles or sample debris by lysing solutions and thorough washing. After washing, the sample is exposed to another solution to denature the DNA in situ. The denaturing solution is followed with a neutralizing treatment.

The matrices are then rehydrated with the solution containing primer, nucleotide and polymerase molecules. The DNA is amplified by rounds of primer extension of target DNA. A short time is allowed for annealing of one or more primer pairs (a pair is defined as two primers that border opposite ends of a linear target DNA and are complementary to the opposite DNA strands) at an appropriate temperature. The temperature is changed to the optimal temperature for polymerase activity for a time period long enough to extend the DNA segment past the sequence to which its primer pair partner binds. The temperature is raised to a denaturation temperature for the DNA during a simultaneous partial dehydrating period. A new round is initiated by rehydrating with pulses of fluid to rehydrate the gel and the temperature is lowered to the annealing temperature. Each amplifying round theoretically increases logarithmically the copies of DNA target segments; the actual increase depends upon the efficiency of the polymerase. Approximately twenty to twenty-five rounds of amplification increase one DNA copy to two million copies, which is more than the number of copies needed for detection by current labeled probes. The number and choice of primer pairs and the number of replication cycles will vary according to the target nucleic acid. The sequence of a target nucleic acid must be known to determine a system to be used for detection. As more sequence information becomes available, the choice of primers for any one system may be changed to reflect a conserved genetic region and improve the specificity of detection. New technology may improve fidelity of primer annealing and DNA polymerization to allow accurate detection by incorporating labeled nucleotides in the amplification step, thus eliminating the need for a separate hybridization step in the detection process.

The gel matrices are dehydrated after the gene amplification reaches the level needed for detection by the hybridizing probe. The hybridizing probe consists of single-stranded DNA complementary to, but shorter than, the DNA target sequence and has one or more label molecules attached. The choice of nucleotide sequences for the hybridization probe reflects the same considerations stated for primer sequences. The hybridizing solutions are pulse-sprayed into the reaction chamber. The shorter DNA probes diffuse and bind to the amplified copies within the matrices, but the diffusion conditions retard the leaching-out of the longer, amplified segments.

An alternate procedure involves primer pairs back to back along a target sequence in order to extend longer targets efficiently. The number of primer pairs in a linear or nested series may vary to accommodate the size-length of DNA required to immobilize the amplified segments during treatment. This alternative requires a ligase to incorporate each primer covalently to the linear molecule at its 5-prime end and the ligase needs to be thermo-resistant. In a particular system, such an enzyme would need to be isolated from nature, if it has not been already isolated.

Another alternate procedure involves adding the hybridization probes during the amplification phase. When single-stranded, labeled probe molecules are incorporated into the growing chains, they become part of the amplified DNA and sequential hybridization is not necessary. Since the process time is dramatically reduced in simultaneously amplifying and labeling the DNA, this step is desired. An enzyme for joining single strand nicks as described in the preceding paragraph is also necessary in order to insure the target sequence was labeled unambiguously over a background of randomly-primed, amplified DNA.

Each kind of labeled probe that hybridizes to the target DNA is detected according to the nature of its label molecule. The number of aggregates of detection signals corresponds to the number of original target sequences directly. In the case of higher density of targets or remelted agarose, the number can be interpolated.

In a broad aspect, the device of the invention comprises:
a top piece and a bottom piece, said bottom piece having
a matrix holding area, said top piece having a closed position;
said top piece and said bottom piece hinged together along a first side of said bottom piece, said top piece having a first area that extends beyond said first side, whereby downward pressure on said first area causes the top piece to hingedly move away from the bottom piece and upward from the closed position to an open position; and
said bottom piece having an overlap area on a second side of said bottom piece, said overlap area extending beyond said top piece, said overlap area having a fluid receiving depression, whereby fluid added to said fluid receiving depression may diffuse into matrix material placed in said matrix holding area.

The bottom piece and top piece are preferably parallel to each other except where the matrix is not of a uniform thickness.

In more detailed aspects of the device of the invention, the "first side" of the bottom piece may be an end or a long side of the preferably elongated bottom piece. Thus, in a first embodiment of the carrier device of the invention the top piece is hinged to the bottom piece along a short edge of said bottom piece and towards the short edge of the top piece, and said first side is opposite and parallel to said second side.

In a second embodiment of the device invention, the top piece is hinged to the bottom piece along a side edge of said bottom piece and said top piece, and said first side is perpendicular to said second side.

The method of the invention utilizes the device of the invention. The sample to be analyzed for the presence of a particular DNA component (or RNA or polypeptide moiety) is suspended in matrix material placed in the matrix holding area of the device. Any one or more of the following steps may then be performed on the matrix and suspended sample, depending on the sample and the results desired: (a) removal of undesired components, e.g. cell wall material, proteins, etc., (b) amplifying a desired nucleic acid component in the matrix material; (c) applying an electric current to the matrix material; and (d) hybridizing a labeled probe to a desired component. Subsequent steps known in the art may be used to detect the particular component in the matrix, or the component as amplified and/or labeled in the matrix.

The device of this invention facilitates automation of DNA-based diagnostics and genetic surveillance and detection. Although the discussion and examples herein are directed primarily to DNA analysis, it is clear that the device of the invention may be used with RNA with equal facility. The device of the invention serves as the specimen container. It can also serve as a mold for embedding a specimen in its matrix. It serves as a specimen holder for manual and mechanical handling and transport. The device serves as an individual archival record for each sample specimen. The sample nucleic acids are preserved in such a way that they may be tested more than once, or the sample may be analyzed for the presence of other nucleic acid targets.

Its parts are configured to open and close via a hinge connection. The closing mechanism may be incorporated into the automated instrument (for automatic gene processing and detection according application Ser. No. 07/227,348, abandoned in favor of continuation application Ser. No. 071,935,637), which has been abandoned in favor of file wrapper continuation application Ser. No. 07/935,637filed on Aug. 24, 1992 which opens and closes the hinged parts. Said application is incorporated herein by reference. The invention may also be opened and closed manually.

One way the invention is different from other diagnostics is that in the invention nucleic acids in specimens, may be dispersed randomly in the matrix, and detected as individual targets in the specimen. The significance of this format is that target nucleic acids in the dispersed cells or viral particles are enumerated in order to quantify the number of cells or viral particles containing the suspected target DNA. A given degree of amplification of target DNA in a matrix will distinguish locations that represent a few copies of original target from many copies of target. The difference in amplitude of these signals, and construction of a total signal by summing individual signals, reflects a more accurate quantitative answer for each specimen as opposed to measuring a single amplitude for total signal of each specimen. In addition to improving measurement of signals over background noise, the method is useful to distinguish individual particles/cells having a few copies of a target DNA from those with many copies. This information can be predictive (1) in cancer when in vivo gene amplification means a more aggressive malignancy or (2) in viral infections to distinguish latent from active infection.

DNA sequences are excellent molecular probes because of the complementarity of primer and probe sequences to target DNA for the purpose of amplification and hybridization. Similarly the recognition sites of restriction endonucleases are DNA-sequence specific. Restriction fragment length polymorphisms (RFLP's) are the result of restriction endonuclease cleavage and require electrophoretic size fractionation. Detecting a particular sequence variation may indicate individual identity, disease susceptibility or disease state.

The purpose of the electrical current in electrophoresis within the device of the invention is to fractionate and concentrate the macromolecules by size. In the case of nucleic acids, either specific restriction endonucleases, ribozymes (non-protein RNA molecules that cut and resplice RNA into genetic messages) or polymerases may be introduced into the gel matrix to act upon the nucleic acids, which are selectively embedded. "Selectively embedded" means that the nucleic acids of specimens are trapped and other cell components are washed away. Experiments have shown DNA sequences of a few hundred nucleotides or more remain essentially immobilized during amplification and hybridization conditions in given matrix materials while allowing short oligonucleotides, mononucleotides or enzymes to diffuse as necessary. The endonucleases break linear DNA into restriction fragment polymorphisms. Polymerase molecules, together with DNA primers, are used to expand a selected DNA or RNA fragment population. With addition of electrical current, the fragments move through the gel matrix toward the anode, according to their size. Subsequent staining or hybridization within the matrix and carrier enables the identification of specific band patterns. Amplification products may be identified by electrophoretic separation and non-specific DNA staining; but in some cases hybridization probes are necessary to distinguish them from spurious amplification products which cause ambiguities.

Electrophoretic mobility of specific DNA restriction fragments, RNA messages or amplified nucleic segments are then compared with those similarly treated from another specimen. For example, specimens from two or more individuals may be compared for paternity identification. Forensic specimens may be compared to specimens from suspects. Family groupings may be compared for markers of genetic disease. Tumor specimens may be compared to standards for classification.

The electrophoretic character of this device is different from other electrophoresis equipment in that the macromolecules in the matrix are automatically processed before, after or in between electrophoretic phases. Different fluid treatments are applied automatically in series to the matrix carrier. The ability to automatically change the solution saturating the matrix heretofore was not possible. The instrument in my co-pending patent application provides processor-controlled fluid delivery to individual matrices. An equivalent electrical current is supplied to each matrix carrier in each rack by design of the circuits.

Previously, multiple specimens were grouped in the same matrix for simultaneous electrophoretic comparison. In this invention, specimens contained in each matrix are processed and compared with both a standard-,built into each matrix and a standard matrix processed with each instrument operation. A matrix carrier manufactured with quality control standards is another advantage of the automated system. The electrical resistance of each matrix will be reproducible when it is saturated with standard buffer. Advantages of the automated handling and separating of specimens into multiple matrices are (1) standardization of accurate assay results (2) less technician skill and less technician preparation and handling time required and thus lower test cost (3) more convenient sample collection and (4) less human error in switching samples or labels. Current methods require a technician to prepare a sample and transfer it to another container or a gel together with other specimens. A specimen may go through several container changes during processing, and each container change is a possible source of error in identifying a patient specimen or sample source. The matrix carrier in this invention contains the patient specimen or sample throughout the entire processing.

In standard electrophoresis the prepared sample is manually loaded in the gel for electrophoresis, and the gel, or the nucleic acids in it, are manually handled for hybridization and detection. The feature of the matrix carrier of the invention is that the physical and chemical handling of it is automated within the instrument. Other gel matrices molded in a carrier are removed from the carrier for staining or further processing. This carrier is unique in that it can be opened and closed mechanically by the instrument in coordination with the fluid and air flow systems in the thermal chamber of the instrument. This feature allows the genetic specimen to undergo further treatments without transfer to another vessel.

Furthermore, the automated system represents versatility in applications. A unique matrix carrier is intended for each specific diagnostic or DNA identification test. Matrix size and composition will be adapted to perform a particular kind of assay. Racks are designed to hold matrices of the same design. The same basic instrument design will hold any rack configuration and accommodate processing for any of the tests. It is also clear that instead of or in addition to using the carrier for electrophoretic separation of DNA or RNA, the carrier may be used for analysis of sample proteins using standard electrophoretic techniques or in situ histochemistry.

Sequence-specific nucleic acid identification depends upon one or more of three fundamental methods: amplification, hybridization and electrophoresis, all of which may be performed using a matrix carrier according to an embodiment of the invention. The automated system for DNA-based diagnostics herein incorporates one or more of these methods in a given order depending upon the nature of the specimen and the quantity of nucleic acid in a particular type of specimen. Microprocessor-controlled processing starts with a sample preparation phase. Lysing and deproteinizing treatments are performed automatically to prepare the sample specimen after it is incorporated into the matrix carrier and loaded into the instrument as discussed in application Ser. No. 7/227,348, abandoned in favor of continuation application Ser. No. 07/935,637. The application of treatments that follow are programmed to perform methods appropriate and prearranged for a batch of similar matrix carriers.

As illustrated in the schematic of FIG. 9, the automated system has great flexibility. After sample preparation any one of the three fundamental methods are performed first: amplification, hybridization or electrophoresis. Detection of the sequence-specific nucleic acid target may occur after treatments for any one of the methods. A particular test can involve one, two or all three methods before detection, in any order.

The invention includes any possible coating of the carrier surfaces with selected biomolecules, natural or synthetically-manufactured, by chemically attaching them to surfactants which normally adhere to the carrier material. For carriers made of glass, a known (standard method of binding biomolecules is with sulfonyl chlorides (Nilsson et at., In W. B. Jakoby (Ed.) *Methods in Enzymology*, Vol. 104, 1984, Academic Press, Inc., Orlando, Fla). For carriers made of polypropylene or polystyrene, chemical attachment may be by hydrophobic binding to their phenyl groups. The purpose of preadhering molecules to the carrier is to facilitate the processing of genetic detection.

For a fuller understanding of the nature and objects of the invention reference should be made to the following detailed description taken in connection with the accompanying drawing figures.

BRIEF DESCRIPTION OF THE DRAWINGS

FIG. 5 is a perspective view of a second embodiment of the invention in a closed position.

FIG. 6 is a perspective view of the second embodiment of the carrier of the invention in an open position showing a side hinge and subsections of a matrix.

FIG. 9 is a schematic diagram showing some of the various analyses and methods for which the invention may be used.

DETAILED DESCRIPTION OF THE INVENTION AND PREFERRED EMBODIMENTS THEREOF

Figure 1:
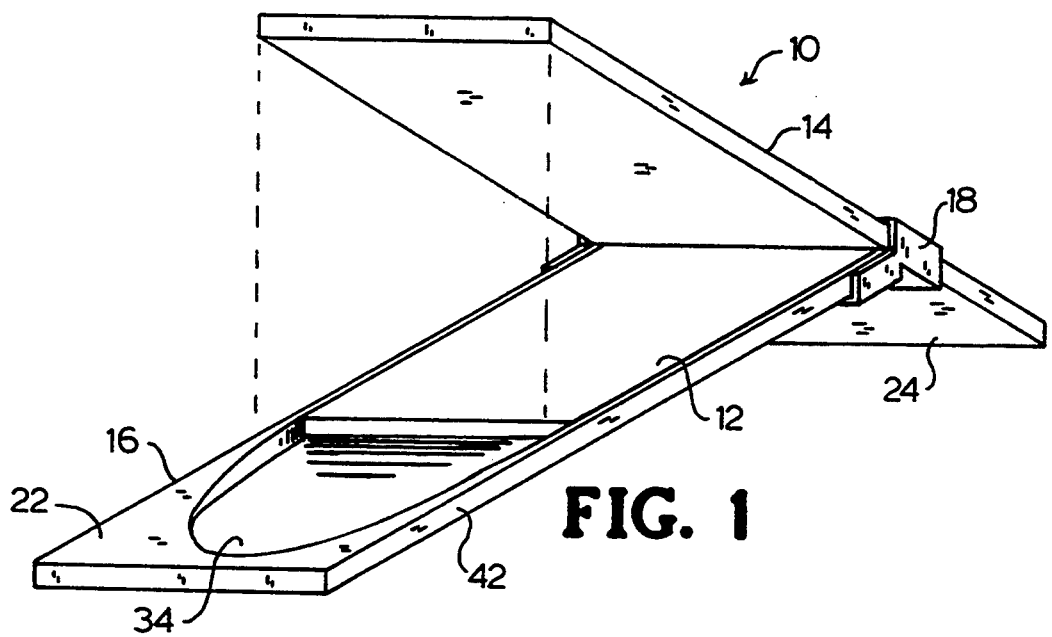
FIG. 1 is a perspective view of a first embodiment of the carrier of the invention in an open position.
Figure 2:
FIG. 2 is a side view of the first embodiment of the carrier of the invention in a closed position.
Figure 3:
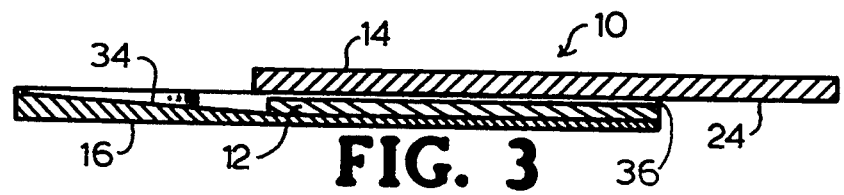
FIG. 3 is a side view of the first embodiment of the carrier of the invention with carrier edge removed showing the matrix space and the channel.
Figure 4:
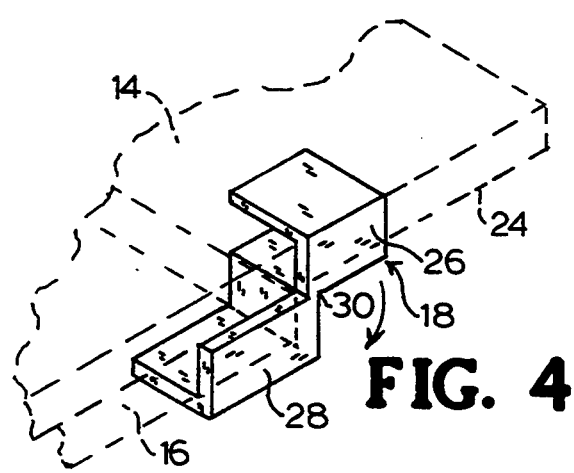
FIG. 4 is a perspective view of a hinge of the first embodiment.

The invention broadly comprises a carrier 10 and a matrix 12 capable of containing biological specimens. The carrier 10 is composed of an upper rectangular piece 14 and a lower rectangular piece 16 hinged together; which, when folded, encase the matrix 12 and, when unfolded, expose one surface of the matrix 12.

Two embodiments of the invention are depicted in the figures. Both embodiments may have the electrophoresis electrical contacts, multiple matrix sections and subsections, but for ease of depiction, these variations are not shown in both embodiments.

In a first embodiment (FIGS. 1–4) the hinges 18 are along a shorter side of the lower rectangular piece 16, while in the second embodiment (FIGS. 5–7), the hinges 18 are along a portion of a longer edge of the lower rectangular piece 16. Having the hinge 18 along a longer side portion of the lower piece 16 (second embodiment) is valuable for electrophoresis, where a longer matrix is preferred. Such a side hinge arrangement allows a longer, narrower matrix while requiring less overhead space for opening the carrier than an elongated cover for a carrier that was hinged at an end would require.

The edges of the two pieces 14 and 16 are juxtapositioned to overlap each other so that in the first embodiment (FIG. 1) the upper piece 14 overlaps and extends beyond the lower piece 16 at the end having the hinge 18, and the lower piece 16 extends beyond the upper piece 14 at the end of the carrier 10 that is not hinged. In the second embodiment (FIG. 5), the upper piece 14 extends beyond the lower piece 16 at the hinged side of the lower piece 16, and the lower piece 14 extends beyond the upper piece 14 at an edge perpendicular to the edge having the hinge 18.

The lower overlap 22 on the lower piece 16 functions to receive fluids which may diffuse into the matrix 12 whether the invention is in the closed or open position. The upper overlap 24 of the upper piece 14 functions as a lever end to open the invention. Mechanical pressure applied to the upper overlap 24 lifts the upper piece 14 away from the matrix 12, which rests on to the inner surface of the lower piece 16.

Each hinge 18 (FIG. 4) in the first embodiment preferably comprises an upper portion 26 grippingly engaging the upper piece 14 of the carrier and a lower portion 28 attached to the lower piece 16. The means of attachment may be glue or other known means of attachment. A flexible bend area 30 located between the upper portion 26 and the lower portion 28 enables the hinge movement and the opening and closing of the carrier 10. The hinge 18 may be made of flexible plastic, or may be made of a rigid material such as a plastic or metallic alloy, except in the flexible bend area 30. Preferably such a hinge is attached at each side of the carrier 10. Although the carrier is described as comprising separate pieces, it is equally possible that the carrier may be molded as one piece with a "living" plastic hinge connecting the portions or that two or more components of the carrier may be molded together.

Treatment solutions from fluid lines 32 in the device of the co-pending application flow or drip into channel(s) 34 on the lower piece 16 and diffuse into the matrix 12. The fluid system as described in my co-pending patent application delivers measured volumes from one of multiple reservoirs through a common line either in a continuous or pulse mode at a selected flow rate.

A system of valves controls selection of the treatments that will diffuse though the matrices. The valves operate in the connections between the reactor chamber and the reservoirs which hold the reagents. A water line connects to the system through a valve and a regulator limits the maximum pressure. The pump is activated for auxiliary pressure if the water pressure reaches a designated lower limit. The system also includes blowers and heating elements to control the air or fluid temperature in the chamber. Fluid application is also important in opening and closing the carrier halves 14 and 16. Application of a fluid volume at the time of opening releases surface tension between the upper piece 14 and the matrix 12. This action reduces the mechanical force required to separate the upper piece 14 from the matrix without disturbing the matrix 12. Application of fluid to the matrix 12 prior to closing the carrier pieces 14 and 16 leaves a liquid film between carrier piece 14 and the matrix 12 upon closing. Closure of the carrier 10 at the hinged joint 18 brings the surfaces that are closest to the hinge 18 together first and gradually those farther away from the hinge 18 make contact. The wave-like closing action smoothes out the bubbles whose presence may cause aberrant test results.

The fluids from channel 34 saturate the matrix 12 and fill the space between matrix 12 and the upper half of the carrier 14, and excess liquids may exit at the opening(s) 36 between the hinged pieces 18. Collecting troughs on the racks and the shelf below the racks within the instrument provide for fluid disposal (not shown). Any opening(s) along the edge are plugged during addition of the matrix material to the carrier 10 when the carrier is being prepared for use until after the matrix 12 has been formed. Taping the opening(s) may be used to close them, but other means of temporarily covering the opening are possible. The tape or other fastener is removed when the carriers 10 are loaded in a rack, or a sealed barrier over the opening(s) may be broken by the opening or closing action of the carrier pieces 14 and 16.

Opening 36 between the hinges 18 or an open side or end of the matrix 12 also allow electrical contact with the matrix material. The electrical contacts 38 and 40, in each embodiment and shown for the second embodiment in FIGS. 5 and 6, permit a constant or deliberately variable electrical current to flow through individual matrices in order to optimally resolve different size classes of macromolecules. A coating with negatively charged groups such as Nafion TM (DuPont Co., Wilmington, Del.) on the lower surface of the upper carrier half 14 and/or the upper surface of the lower carrier half facing the matrix 12 may be used to help reduce electroendosmosis, in which cations in aqueous fluids and hydrogels tend to flow toward the cathode.

The carrier pieces 14 and 16 may be made of glass or plastic or combinations thereof, sheets of polymer (such as polyetherimide, Ultem TM, General Electric, Pittsfield, Mass.) or metallic alloys. Carriers used for assays involving electrophoresis are made of non-conducting materials in order that current flows through the matrix and not the carrier. Parts of the carrier may be made of optically clear material for scanning the matrix.

The matrix 12 is preferably a semi-solid material made with agarose or acrylamide or similar polymer, or mixture thereof, that incorporates several times its weight of an aqueous solution (hydrogel). A liquid specimen or specimen mixed with a liquid diluent may be added to the carrier at channel 34, or into subsections 48 directly, from where it either combines with a liquid matrix 12 or diffuses into a pre-formed dehydrated matrix or a subsection thereof. Application of heat or a polymerizing agent incorporates the specimen into the matrix 12 or subsection thereof, forming a gel matrix with embedded specimen. The gel matrix may be hydrated or not before loading its carrier in the instrument. If dehydrated in storage or transport, the gel matrix material is rehydrated with fluid treatments from the fluid lines 32 of the instrument. A rehydrated matrix, preferably ultra-thin (less than 500 micrometers thick), facilitates diffusion of small molecules and retention of larger ones, quicker electrophoretic resolution and better detection of signal.

If the sample specimen has been fixed on a microscope slide, the slide may be overlaid with agarose or not.

The carrier 10 may be molded to have edges 42 or the carrier halves 14 and 16 may have edge pieces fastened to them. The edges 42 are formed in order to enable molding of the matrix material in a space between the upper and lower carrier surfaces 14 and 16. The space between carrier surfaces 14 and 16 may diverge from one end to the other by placing wedge-shaped edges 42 along the sides in order to form the matrix material thicker at one end (not shown). Such a wedge-shaped matrix may be made by pouring molten matrix material into a wedge-shaped enclosure formed between the upper and lower carrier surfaces and bounded by edges 42. The purpose of the wedge configuration is for increasing the electrophoretic separation of a wider range of nucleic acid fragment-size classes over less linear space.

Another aid to better resolution of fragment populations is variation of the concentration of the matrix material over the linear path of electrophoresis, i. e., making a gradient gel matrix. When matrix material is preformed on carrier half 14 or 16, it may be applied in a manner to form a concentration gradient and/or wedge across one dimension for better electrophoretic resolution.

Edges 42, and extensions 44 which may overlap the surface of the lower carrier section 16, are molded or fastened to one or both of the carrier halves. Edges 42 and extensions 44 may form molds for matrix materials, with and without added specimen material. They may be designed to mold either matrices 12 of uniform thickness in the space between the upper 14 and lower carrier 16 surfaces or mold subdivisions of the matrices 12 that contain different matrix materials, volumes or concentrations thereof (FIGS. 5 and 6). The edge 42 in FIG. 6 is shown cut away where electrical contact 38 crosses it. The extensions 44 may form molds 46 on the lower carrier section 16 and subdivide the matrix area into smaller subdivisions. The subdivision of matrices on one carrier allows the different matrix sections to include different specimens or standards.

Introducing the specimen into the matrix allows pretreating the specimen within it to prepare DNA in the sample by a standard method of Smith, Klco and Cantor (1989, In K. Davies (Ed.), Genome Analysis-A Practical Approach, 1989, pages 41–72, IRL Press, Oxford) or by variations of a standard method. In a multisection matrix, another section of the matrix may be pre-formed on the carrier and accept DNA molecules transferred to it from the initial matrix via electrophoresis. The purpose of varying materials, or the volume and concentration thereof, in submatrix sections on the same carrier is to optimize conditions for a specific method. For example, polyacrylamide gel reagents may be introduced, dried and enclosed in one section of the carrier during manufacture. Later, the sample is mixed with liquid agarose and added to the matrix carrier 10 filling subsection spaces 48 and forming subsection 46. After sample preparation treatments and subsequent drying of the agarose matrix in subsections 46, the carrier 10 is opened and electrophoresis buffer applied to all matrix sections. The nucleic acids (or proteins) are electrophoretically transferred from the agarose to the acrylamide matrix (or an intermediate matrix in subsections 54) for a processing step for which acrylamide is better suited than agarose.

The first matrix the specimen encounters may serve to cleanse it. Drying and rehydrating this matrix reduces total volume and thus concentrates samples. Electrophoretic movement of macromolecules from the concentrated first matrix into the second matrix has the effect of loading a more concentrated sample onto the second gel, i.e., more sample target molecules per unit matrix. The more concentrated the macromolecules are when starting electrophoresis, the more easily detected they are after electrophoretic separation due to a narrower band width. The process of this invention overcomes the difficulty of loading enough sample per unit volume on the thin gels. Our research has found that samples migrate from a dried gel to a second matrix.

Research shows further that an added advantage of using a dried matrix is that macromolecules migrate slower in a dried and rehydrated matrix because the pore size is changed by effectively increasing the matrix substance concentration in the hydrogel. We have also observed the percentage shrinkage of a dried and rehydrated flat hydrogel is several times greater in its thickness than in its length or width.

Thus, the advantages of a dried and rehydrated hydrogel are that: (1) it may be more easily manufactured with a lower concentration of matrix material because later drying will increase the concentration; (2) it may be stored dry; (3) the thinner gel may be rehydrated with less buffer volume than a thicker gel; and (4) the thinner gel that results from the drying and rehydration allows better signal detection than a thicker gel. While other hydrogels may be dried before use, this invention permits automatic changes between alternate drying and saturating processes by opening and closing the carrier without removing the matrix or carrier.

The extensions 44 may be raised after the matrix sections are molded. The same mechanism (manual or mechanical, as discussed above) that opens the carrier halves 14 and 16 may serve to remove the extension sections 44 from the matrix 10. When the carrier halves 14 and 16 are opened at the hinge joint 18, the extension 44, which was separating two or more submatrices on the carrier, is no longer positioned between the submatrices. Gel-to-gel or gel-liquid-gel contact allows the parallel transfer of nucleic acids from one submatrix to another by electrophoresis. In the second embodiment, the extension 44 may be opened separately from the opening of carrier halves 14 and 16. Thus, gel matrices on the same carrier may receive isolated treatment or be treated together with any other.

The purpose of two or more matrix sections is to separate functions or samples within one carrier. It is useful when two or more patient specimens are compared in the same carrier or when one matrix section serves one function and the second matrix section serves another function. Examples of different functions are: (1) cleansing nucleic acids in a specimen from interfering biological material; (2) amplifying the nucleic acid fragments; (3) hybridizing a labeled probe to the nucleic acids; (4) fractionating nucleic acids according to size by electrophoresis; (5) comparing an internal standard on the matrix with an unknown; and (6) comparing band patterns to indicate related individuals.

The racks (not illustrated) may hold a number of matrix carriers and are designed in such a way that they position each of the matrices at the opening of a fluid line 32 for fluid delivery from fluid reservoirs as discussed in my co-pending application. The racks are designed to fit into the instrument's thermal chamber. The racks may support the carrier-matrices 10 in any designated plane, horizontal, vertical or diagonal. Tilting the carrier may serve the purpose of increasing the rate of fluid flow when necessary.

The design of racks in which electrophoresis is used will position the matrix in such a way that the matrix completes an electrical circuit. This optional feature that may be incorporated into the automated system of the co-pending application for use of the instant invention is the positioning of electrodes on each rack of a plurality of racks holding the matrix carriers in such a way that applied current can pass through each matrix saturated with an electrical conducting buffer. Positive and negative connections are located on opposite ends of each matrix and connected via contact leads to positive and negative terminal blocks on the rack (FIG. 8).

Figure 8:
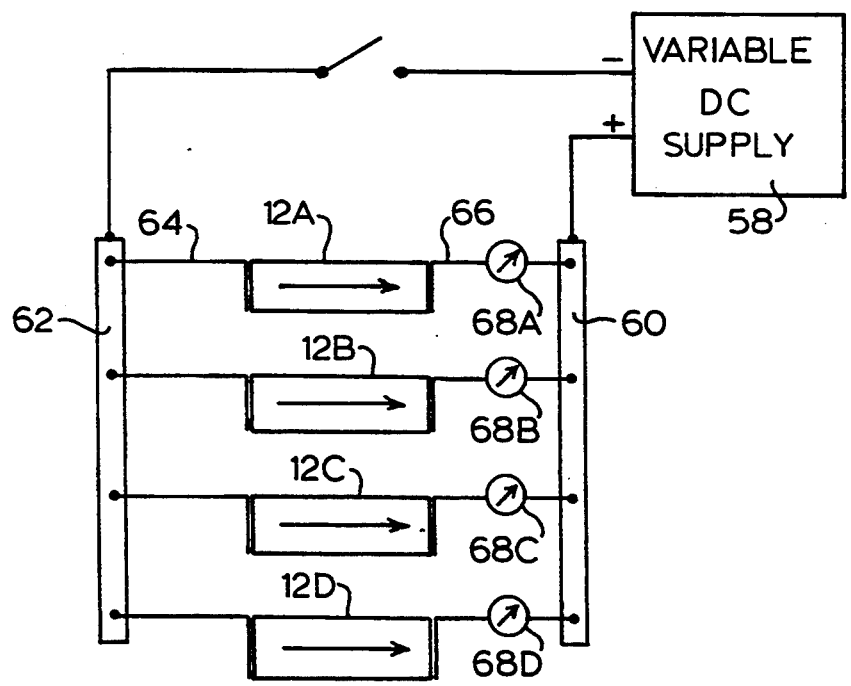
FIG. 8 is a schematic drawing of an electrical circuit closed by a matrix.

In reference to FIG. 8, a variable DC supply 58 has its positive side connected to an anode bus bar 60 and its negative side connected to a cathode bus bar 62. Each electrophoretic matrix 12 of which four are illustrated by way of example, labelled 12A, 12B, 12C, and 12D, is connected on one side to bus bar 62 by way of a lead 64 and on the opposite side to bus bar 60 by way of a lead 66. An ammeter 68 is placed in series with each matrix 12 as illustrated.

In use, the variable DC supply 58 as adjusted to provide an appropriate level of DC voltage and individual monitoring of the current through each matrix 12A, 12B, 12C, or 12D is obtained by monitoring the respective ammeters 68A, 68B, 68C, and 68D. Voltage levels are maintained at levels commonly used for electrophoresis. The ammeter can be connected to an alarm (not shown) so the operator may know if the electrical current is too high, as a backup to discover any inadequate matrices, where there is too great a resistance.

The rack has electrical connections fitting into corresponding connections in the instrument when the racks are in position in the instrument. The rack terminal bus bar is thus connected to a power supply in the automated instrument. The invention so equipped will provide an equivalent electrical current through all gel matrices. In such racks electrical connections from the anode bus bar and cathode bus bar lead to each individual matrix-carrier 10, an anode to one end of the matrix and a cathode to its opposite end. Electrical wire connections are appropriately sheathed with insulating material where no current conductance is desired. Interlocks and lid locks will be placed at all points where an operator may inadvertently come into contact with the electric field.

The air flow system built into the thermal chamber is also used to cool the matrix carriers during electrophoresis and prevent uneven heat build-up. The closed position of the carriers during electrophoresis prevents evaporative loss of buffer from the matrices. The fluid-flow line 32 delivers buffers to the channels 34 to diffuse into the matrices as needed for saturating or cooling them.

The same reaction chamber and rack may be equipped with a mechanism (not shown) to exert a force on the lever end (upper overlap 24) of the carrier. A mechanical platform (not shown) may be equipped with auxiliary heat to raise the temperature of the matrix quickly as it contacts the matrix carrier and lower it quickly when contact is released. A mechanical arm may be equipped with an auxiliary fluid line for delivering reagents or solutions to the matrix carrier different from those supplied through fluid lines 32. The same mechanical arm may be so equipped with a scanning device to read all or a portion of the optical differences on the matrix surface. The purpose of the scanner is convert image data from the matrix to a digital form for computer interface. Either the mechanical arm moves between the rack shelves or the rack moves past the mechanical arm.

The entire sequence of operation is controlled with a microprocessor or programable controller which serves both air and liquid processes. The liquid process begins with the processor energizing an appropriate valve to open, and starting a pump. Transfer of solutions and reagents from reservoirs is accomplished by the pump, which draws liquid into the manifold from transfer lines. The pump valve has its normal connection closed to the pump and closed along the supply manifold. During fluid flow, the pump valve is actuated and the pump draws liquids through the pump and pressurizes fluids in the transfer lines. If pressure as sensed by a pressure switch exceeds the desired limit, a valve opens to a pressure control bypass enough to reduce the pressure by providing an escape route for the fluid from the fluid source being pumped.

Although five reservoirs and five secondary transfer lines are described, it is clear that fewer or more reservoirs may be used. Any of the transfer lines may be further equipped with the capability of injecting specific reagents into the solution passing through it.

The quantity of each solution or reagent transferred from reservoirs to the reaction chamber is controlled by processor activating the pump for predetermined time periods or until the reservoir volume is depleted. The switches that control the valves in the transfer lines are actuated sequentially to provide a series of programmed treatments.

In the preferred use of the embodiment of the device shown in FIG. 1–4, a first reservoir contains a lysing and alkaline denaturing solution; a second reservoir, a neutralizing solution; a third reservoir, the reagents for amplification; a fourth reservoir, the reagents for hybridization; and a fifth reservoir, a hybridization wash solution. A particular reservoir's contents can be changed for each detection system so that custom-made primers (for amplification) and labeled probes (for hybridization detection) can be made for any known target nucleic acid nucleotide sequence. If different tray-rack loads are being treated for different target sequences in the same operation, an optional system of mini-reservoirs may be made available to add different primer probes to each manifold section. Drying cycles and water rinses are programmed between solution treatment sequences as necessary.

The switches for the fans and heating elements actuate and deactuate them separately to provide for different set temperatures in different phases of the dehydrating, amplifying or hybridizing cycles. Thermocouples at strategic locations in the reaction chamber sense a representative matrix temperature and transmit this signal to the microprocessor. As programmed, the microprocessor activates heating elements as necessary to maintain the upper temperature at the desired setpoint for each stage of molecular processing. The fans can produce air flow when heating elements are deactuated to lower matrix temperature quickly. Solutions in the fluid cycle, which are normally cooler than the maximum matrix temperature (for denaturation), may be added to the matrices to accomplish quick lowering of temperature. The coordination of components in both the fluid and air-flow cycles provides the temperature control needed for molecular processes in the detection system.

The process of the invention consists of the following stages: 1) matrix dispensing, sample mixing and DNA immobilization; 2) preparing DNA; 3) amplifying DNA target sequences; 4) hybridizing a labeled probe to the target; and 5) scanning the matrices for signal produced by bound label. The uniqueness of this technology is the stabilization of nucleic acids in a matrix without extensive preparation of the biological sample, and the subsequent treatment of this matrix to prepare and identify the target genetic sequences automatically.

Any biological sample or environmental sample suspected of containing biological material is considered a sample. Each sample is mixed with aliquots of liquid matrix and allowed to solidify. A batch of sample matrices is subjected to subsequent treatments automatically in the reaction chamber 2. Blood, plasma, saliva, cerebrospinal fluid, lymph, urine, homogenous tissue, cell cultures, viruses, water, and soil are examples of sample material, but the process is not limited to these materials. For in situ identification of nucleic acids, tissue sections (prepared by standard methods for microscopy) may be overlaid with liquid matrix placed on tray rack shelves and then treated as other matrices. These matrices may also be scanned microscopically to localize the presence of target nucleic acids in the tissue. Gels containing nucleic acid samples, prepared by standard methods and size-fractionated by gel electrophoresis, may be amplified further and/or hybridized in this system.

The matrix allows entry and exit of reagents by diffusion to expose nucleic acids for identification by nucleic acid hybridization and/or antibody binding. A diffusion pressure is exerted on the gel matrix that maximizes molecular reaction kinetics. The matrix material allows diffusion yet maintains its integrity throughout the treatments that require nucleic acid immobilization. Drying steps during and between some treatments dehydrate the matrix blocks and the subsequent hydration with other liquid treatments enhances diffusion by creating a sponge-like uptake.

The binding of primers and probes requires prior melting of double-stranded DNA (dsDNA). This can be done by either a 95° C. temperature or an alkaline buffer. An alkaline buffer is used in the lysing procedure because it also inactivates biological activity as the DNA is cleansed of cellular constituents. A neutralizing treatment follows the lysing/alkaline denaturing stage. Alkaline conditions do not disturb the agarose matrix but do affect polymerase activity. The isolation and commercial availability of a polymerase that can withstand a brief 95° C. temperature has allowed temperature variation to be the means of denaturing dsDNA in cycles of PCR. The use of thermo-resistant polymerase for PCR in agarose is possible once the gels have been dried and then rehydrated. (A 95° C. temperature does not compromise the integrity of a partially-dehydrated agarose matrix.)

In the second stage the tray-racks of matrices are treated as a unit for processing in the apparatus. The first solution is a detergent/enzymatic treatment to lyse cellular material and solubilize polypeptides and fatty molecules so they may be washed out of the matrix. Alkaline treatment, such as 0.5M NaOH is used to insure lysis and denature the immobilized DNA. Several volumes of wash buffer are diffused through the matrix to clear away biological molecules (except DNA, which is immobilized because of the nature of its structure) and also matrix contaminants (for example, sulfonated groups found in agarose) that might interfere with subsequent enzymatic activity. The wash solution also normalizes pH. The matrices are dehydrated by a drying cycle.

In the third stage the target sequences are amplified. The technology is provided by the PCR techniques. This amplification feature allows the subsequent identification of DNA amplified from one or more genetic sequences per biological. Polynucleotides, custom-designed primers and polymerase enzymes for DNA replication are added in the first solution to enter the dehydrated matrices. The matrices act like sponges to take up the solution. A polymerase chain reaction cycle consists of a) binding the primers, b) extending the DNA chain and c) denaturing the DNA molecules. Each step in the cycle requires a temperature change. Thus, typical temperatures at the three stages would be chosen from the following three ranges respectively, 37°–40°, 63°–72° and 94°–96° C., but other temperatures may be useful for alternate procedures. The cycles repeat until sufficient target sequences are present for detection. The number of cycles necessary depends upon the efficiency of the polymerase and the detection sensitivity of the label being used.

In the fourth stage the hybridization of labeled DNA probe to the immobilized target DNA (RNA) is performed. A typical procedure for hybridizing DNA with labeled oligonucleotide probes is presented in *Methods in Enzymology*, vol. 152, "Oligonucleotide probes for the screening of recombinant libraries," R. B. Wallace and C. G. Miyada, pages 432-442, 1987, Academic Press. Included are protocols for dried gel hybridizations. Prehybridization is not necessary. The dried gel is hybridized in a solution containing 5× SSPE, 0.1% SDS, 10 ug/ml sonicated, denatured E. Coli or salmon sperm DNA and 1-10 ng/ml of labeled oligonucleotides. The gel is hybridized at Td minus 5° or 60° C., whichever is lower (Td is the temperature at which one-half of an oligonucleotide duplex becomes associated in 1M NaCl). The first washes with 6× SSC are at room temperature and then a stringent wash is done at the hybridization temperature minus 5° C. for 1-3 minutes. The unbound probe DNA (RNA) is carefully washed from the matrix without disturbing DNA:DNA (DNA:RNA) hybrid complexes.

In the fifth stage the signal of the bound label is measured with a scanner appropriate for the label incorporated into the oligomer probe. Chemiluminescence, for example, may be detected by a photometer. The location and number of original target molecules present in the sample are reported by the signal. Scanner input data is entered into a microprocessor for matching the sample number with the identity of the sample and for further processing to determine the profile of the total sampled population. Software for the processor enables raw data of the sample to be structured with other information on the sample source and compared to a database.

The following is an example of a reaction protocol using HIV-1 DNA sequences as a representative detection target, the sample tissue being human peripheral blood mononuclear cells:

(A) Mix a sample of whole blood with aliquots of matrix liquid, solidify and load them into the shelves of the tray rack. Load the tray rack into the main chamber.

(B) Connect the reservoirs filled with the proper reagents: first reservoir, lysing solution (0.5M NaOH, 0.1% SDS); second reservoir, neutralizing solution (50 mM KCl, 10 mM Tris, 2.5 mM MgCl2, pH 8.4); third reservoir, primers at 1 uM each, nucleotides at 200 uM, polymerase at about 10 units per sample; fourth reservoir, labeled oligomer probes in hybridization solution based on the procedures referenced above (*Methods in Enzymology*); and fifth reservoir, hybridization wash solution.

(C) Select the proper program for this test and start the instrument's operation. Parameters such as the source of sample tissue and the number and length of target sequences affect the selection of the program.

(i) The microprocessor automatically controls the first two treatment solutions that strip proteins, dry the matrices and leave intact, denatured and neutralized DNA immobilized in the dehydrated matrix.

(ii) The dehydrated matrices are automatically rehydrated with the appropriate reagents for amplification of target sequences of DNA by primer extension in situ. This added solution contains oligomer primers (complementary to a conserved target gene), free nucleotides and polymerase molecules. Choice of primers and probes may change as critical functional domains of HIV proteins are determined and their corresponding conserved genetic sequences are identified.

(iii) Labeled oligomer probes are automatically hybridized to the amplified target DNA in situ and unbound probe is washed away.

(D) Remove the trays and quantitate the number of original target DNA copies present per sample.

The molecular processing is accomplished by processor-controlled commands for the fluid/air flow reactor system which serves the molecular manipulations by providing the necessary microenvironment in the individual matrices. The command system for controlling the microenvironment is chosen for specific gene probe sequences or different types of specimens and consists primarily of duration, pH and temperature of treatments containing standard and custom-made solutions. A user of the system needs only to enter the desired program of treatments into the processor, connect appropriate reservoir bottles to the system, add samples to matrix liquid, load the samples into trays and the trays into the chamber. The processor then automatically selects predetermined appropriate reaction conditions (time, duration, treatment solution, solvent or reagent) for the sample type, and initiates the appropriate commands, in the appropriate sequence, and at the appropriate times to obtain matrix conditions which allow the molecular manipulations.

In the preferred embodiment of the invention, the programing of the number and time intervals of treatments, the endpoints of each treatment, valve-control and electrical switching are computerized into the microprocessor. The system's flexible programming allows use of the device for research and clinical applications in which only one or two of the phases are required. Some examples of the different uses are preparation of large-sized DNA or intact chromosomes from cultured cells or organisms for other DNA manipulations, amplification of target DNA for other DNA manipulations, probe hybridization in gels in which nucleic acids have been size-fractionated by electrophoresis, or in situ amplification and hybridization of nucleic acids of tissue sections for microscopy. If the RNA in the sample is the target to be amplified, the sample is treated with reverse transcriptase to make a nucleic acid complement of the RNA just prior to the amplification step.

The scanning of the identification signal of the target sequence is incorporated into the final stage (D). The tray rack assembly enters a scanner and exposes the flat surface of each matrix to a scanner, which reads the signals. The scanning apparatus is interfaced with the microprocessor to give quantitative (location of signal) and qualitative (strength of signal) measurements. A representation of signal measurements made in situ may be printed out.

In the following examples, amplification is defined as a means to biochemically increase the target nucleic acid mass. Target nucleic acid means those molecules containing a designated genetic sequence. Separation of nucleic acids by size utilizing electrophoresis is performed in a hydrogel supplied with an electrical current. Hybridization refers to the binding of complementary nucleic acids sequences, one partner of which carries a label whose signal can be detected. If amplification is used alone or follows hybridization it is understood that the primers or sequences used in binding targets or nucleotides for amplification may also carry a label.

It is further understood that automated processing begins with sample preparation and ends with the test results of detection. It is further understood that standard reagents and reaction conditions may be used for the various sample treatment steps, such as amplification, electrophoresis and hybridization. The following examples are presented to iterate the ways in which the methods that are diagnostic of nucleic acid sequence-specificity may be interchanged or combined in the processing. In the following examples, the specimens in sections 46 are combined with matrix material which might be agarose; sections 54 are pre-formed in the carrier and may be different compositions to amplify different targets. Polymerase chain reaction (PCR) is shown in the preferred method of amplification when amplification is used, but amplification methods are not limited to PCR. Our research demonstrated amplification in agarose gels by PCR with Taq polymerase. The addition of more primer molecules during PCR as they are used retards formation of undesirable primer dimers. Although not discussed in detail herein, standard techniques including immuno-staining for analysis of polypeptides or other cellular components in gels may be performed with the device of the invention.

EXAMPLE 1

Matrix and Carrier for Sample Preparation, Amplification and hydridization

The initial process of sample collection involves randomly distributing specimen in diluent if the sample is too concentrated for analysis, and then combining it with a liquid matrix material or a pre-formed matrix in the carrier.

The order of treatment methods in this example are sample preparation, amplification, hybridization and detection. This application would be used in a diagnostic in which amplification with specific primers yields discrete products from non-targe DNA, some of which may even be in the same size class as the target DNA. These products can be discriminated by hybridization from target sequences. In particular, this protocol may be used for detecting proviral sequences of human immunodeficiency virus type 1 or human T-cell leukemia virus type 1 where these other products have been reported (Abbott, M. A., B. J. Poiesz, B. C. Byrne, S. Kwok, J. J. Sninsky and G. D. Ehrlich. 1988. Enzymatic gene amplification: qualitative and quantitative methods for detecting proviral DNA amplified in vitro. *J. Inf. Dis.* 158:1158-1169.).

If the specimen is a sample from blood or another body fluid, a measured amount may be added directly to the matrix 12 through the channel 34. The matrix carrier 10 is processed by heat or chemicals to embed the specimen in the matrix 12 and render it non-infectious. The matrix carrier 10 is closed during transfer to the instrument site, where it is loaded, along with others, onto a rack and placed in the thermal chamber of the instrument. The fluid delivery system sequentially supplies multiple reagents in series through an individual fluid line 32 to each matrix-carrier. Thus, a lysing-sample preparation solution from the fluid line 32 flows into the channel 34 on carrier section 16 and diffuses into the matrix 12 and is used to remove non-nucleic acid components in the sample. The carrier is mechanically opened as the solution reduces surface tension between the upper matrix surface and the carrier piece. The final solution of sample preparation rinses away previous solutions and forced, heated air of the thermal chamber dries the matrix with the carrier still open.

The amplification solution and reagents are then added through the fluid line 32 to rehydrate the matrix. The carrier closes during amplification temperature cycling to prevent evaporation. After amplification the carrier opens to facilitate rinsing and adding hybridization solutions. The carrier closes during hybridization to an enzymatically-labeled nucleotide probe and opens again for the stringency washes, and subsequent addition of substrate and buffers for detection. After substrate development the carrier closes for reading by a scanning detector. One possible detector may be an optical array for measuring transmitted or reflected light differences that distinguish positive signals over background noise. The scanning is not limited to detecting enzymatic activity on a chromogenic substrate, but other labels, such as fluorescence may be used.

Data from amplification and hybridization experiments with the matrix covered and uncovered indicate opening and closing of the carrier is critical to facilitate either rinsing or drying of the matrix in the open configuration and controlling evaporative loss during reaction periods in the closed position. Experiments which were performed in a covered or closed matrix had retarded diffusion of treatment solutions, and retarded rinsing and drying the matrix. Water evaporation from the matrix in an open carrier leaves behind more concentrated solutions which affects desired enzymatic activity. If the matrix dries out during hybridization, signal noise increases. A carrier-fluid-matrix interface at the surfaces of the matrix appears to be important for molecular diffusion when the carrier is closed. One reason drying the matrix before amplification and hybridization is important is that drying causes the matrix to shrink and consolidate the nucleic acid molecules into a smaller volume. Agarose does not rehydrate to its original volume so less rehydrating solution is required and thereby fewer primer or probe molecules are needed to maintain an adequate molarity. A dried agarose matrix soaks up reagents like a sponge, hastening diffusion of necessary biomolecules. The ability to open and close the carrier during processing as allowed by the carrier of the invention has been found to serve the above multiple purposes.

In the case of a genetic disease caused by a single base mutation such as cystic fibrosis, the purpose of a diagnostic is to determine the presence of mutant alleles either as homozygous or heterozygous genes. Here amplification of the target DNA or RNA means fewer specimen cells are needed. After sample preparation and amplification, hybridization with the appropriate labeled oligonucleotide probes, under stringency conditions which distinguish either the single base-pair match or mismatch, will be sufficient for detecting the disease or carrier state.

EXAMPLE 2

Matrix Carrier Design for Sample Preparation, Amplification and Electrophoretic Separation In this example, the sequence of methods is sample preparation, amplification, electrophoretic separation of amplified fragments, and detection by staining of fragments and scanning resulting bands for interpretation by image analysis software. This example illustrates the value of matrix subsections and racks designed with electrical bus bars leading to each matrix.

Figure 7:
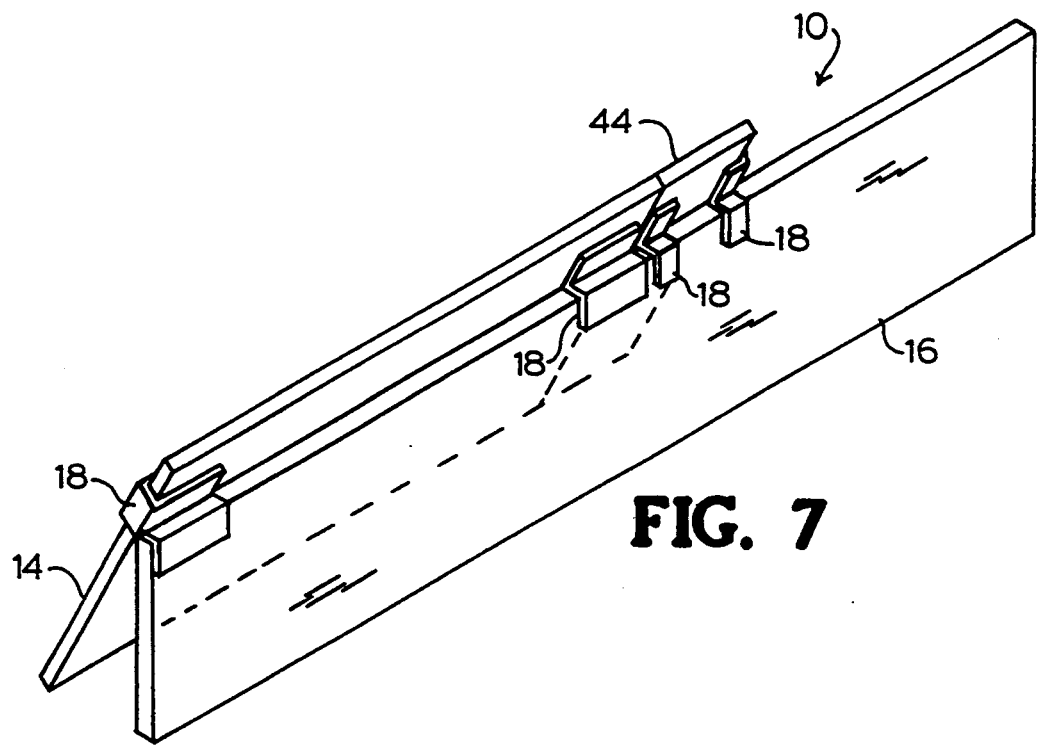
FIG. 7 is a back perspective view of the second embodiment of the invention showing the hinge.

An example of a subdivided matrix is illustrated in FIGS. 5–7. A mixture of specimen and matrix material is added to form subsections 46 of matrix 12. Although three subsections are shown, this amount maybe varied for particular uses. The fluid lines 32 are supplied by the fluid delivery system of the instrument in my application Ser. No. 07/935,637, a continuing application of Ser. No. 07/277,348 filed Aug. 2, 1988 now abandoned. Carrier extension piece 44 is raised after the matrix and specimen subsections are set. Sections 46 are treated with fluids from fluid line 32 in order to make nucleic acids from particles/cells in the specimen more available for modification or detection and to,reduce interference from non-nucleic acid molecules. The hinged edge of extension piece 44 has an opening(s) in order for fluids collecting around subsections 46 to drain off into troughs on the racks.

The contents of sections 54 and 56 are protected between the carrier halves 14 and 16 in the closed position or by the barriers formed by edge extensions 44. The treatment solutions from the fluid line 32, used for lysing and washing the sample, do not enter the enclosed sections 54 and 56. After sample preparation is complete in subsections 46, the instrument automatically opens the carrier enabling fluid to enter matrix sections 54 and 56. This fluid is an ionic buffer that permits DNA to migrate towards the anode when current is applied.

Current is supplied from leads from the bus bar fastened to the shelves of the rack in such a way that each matrix placed on the rack comes into electrical contact with leads of opposite polarity, and when saturated and current is applied, the matrices close parallel circuits. An electrical current flowing through the buffer-saturated matrix-coated carrier, as shown by the arrows on FIG. 8, causes the nucleic acids from the specimen in sub-sections 46 to migrate into subsections 54.

Preformed matrix subsections 54 may hold different primer sets for amplification of different target fragments in duplicate specimens, or a subsection 54 may contain known DNA standards. These designated primer sets could be immobilized in sections 54 at the time of matrix-carrier manufacture. After the first electrophoresis, the fluid line 32 supplies sections 54 with amplification buffers to supplement what reagents are already incorporated in them. Controlled temperature cycles allow treatments from fluid line 32 to enzymatically amplify a specific,target DNA sequence in closed carriers. The carrier may be sealed in manufacture with a polyethylene film to cover matrix sections 54 and 56 and prevent contact with aqueous fluids from channel 34. Once the carrier is opened, the seal is physically separated so that subsequent closing of the carrier allows fluids to be drawn through the carrier halves when closed.

The second application of current allows the DNA molecules, including the amplification products, to migrate into section 56. In cases where primers were reversibly immobilized in the preformed matrix subsections, a treatment step to release them is included. Section 56 is also a preformed matrix of still a different composition. The composition of section 56 is selected to resolve different-sized fragments Pre-amplified products can be typed following separation by electrophoresis. In Allen et al. the authors present an polyacrylamide gel system to improve the resolution and staining of polymerase chain amplification products. Large-pore size, ultrathin layer, rehydratable polyacrylamide gels were prepared by standard methods of varying concentrations of polyacrylamide and cross-linker to select a desired pore size. A buffer system was employed which rehydrates the gel in a buffer containing sulfate ions for horizontal electrophoresis at 20° C. with borate counterions introduced into the rehydrated gel slab from gel plugs overlaid on the gel slab. The composition and buffers chosen could be as described by Allen et al. (Allen, Robert C., G. Graves and B. Budlowe; 1989; Polymerase Chain Reaction Amplification Products Separated on Rehydratable Polyacrylamide Gels and Stained with Silver; Biotechniques 7:736–744) comprising a 5% T wedge rehydrated polyacrylamide gel and discontinuous buffer system. The molarities suggested with respect to the ions are 0.0175–0.035M sulfate and 0.141M borate. In a discontinuous buffer system a sulfate-leading ion made by adding $H_2SO_4$ in a buffer may be incorporated into the cathodal end of the section 56 matrix and the borate-trailing ion incorporated into the overall section 56. The ions may be supplied by prior incorporation of one into the matrix section with the other supplied by fluid line 32 at the time of electrophoresis. In instances where ionic buffer salts are incorporated in the matrix 56, adding deionized water through fluid line 32 will sufficiently hydrate the matrix to supply the buffer requirements. In other instances buffer prepared at its final concentration is supplied through fluid line 32.

After the electrophoretic separation of DNA fragments, the carrier halves are opened to permit staining solutions to diffuse into section 56 and stain fragments for visualization. The fluid line 32 supplies staining solutions. DNA identification in this case results from comparing bands representing the electrophoretic mobility of an expected target fragment size-class to standards and/or other specimens. In this example all nucleic acids present in the matrix are stained and the preferred method of staining might be silver staining according to the modification of Allen et al. in which polymerase chain reaction amplification products are separated on rehydratable polyacrylamide gels and stained with silver which detects 10 pg/mm band widths (Allen, R. C., G. Graves and B. Budowle, *BioTechniques* 7:736–744, 1989). The staining process is developed to an optimal level. Allen et al. state "the major advantages of this electrophoretic system, compared with submarine gel electrophoresis are 1) the rehydratable polyacrylamide gels may be stored for several years before use at room temperature; 2) the gels may be rehydrated with buffers or ampholytes at the ionic strength of choice; 3) reduced band width of the separated DNA is readily achieved with zone sharpening in the absence of electroendosmosis; 4) there is no significant shift in zone position over at least 100-fold concentration differences of the same DNA sample, and 5) each separation may be preserved as a dried silver-stained gel, which serves as a permanent record". The authors further state that restriction fragment length polymorphism (RFLPs) and amplified fragment length polymorphisms (AMP-FLPs) can be useful procedures for the genetic characterization of biological specimens. The carrier halves are closed after staining treatments to flatten the matrix in one plane for scanner reading. A mechanical arm passes the carrier half that is transparent by either movement of the arm or the rack. The mechanical arm might contain an arc light as a light source, lenses for focusing or intensifying light, and an optical array for detecting either transmitted or reflected light. The intensity of the light source and the speed of the pass can be varied to produce the best signal-to-noise ratio and be set to an internal standard matrix before reading the other matrices.

Examples 1 and 2 demonstrate the use of designated matrix carriers in the automated system, the first one being a viral diagnostic test and the second being a DNA identification test. A specialized carrier enables many functions to occur on an individual carrier which is processed automatically along with others in the same fashion. In the second example, closing the matrix halves is critical in protecting a matrix subsection during prior treatment to another subsection and opening is critical in permitting rehydration of a preformed matrix. The fluid delivery system supplies different reagents through a common fluid line to individual matrices. The DNA from the specimen in the second example migrates from one subsection of the matrix carrier to another by electrophoresis. Subsections 46 are thicker than 54 in order to prepare the sample in a larger matrix volume and then concentrate it by drying. Experiments performed with the carrier of the invention demonstrate that fragments will migrate through dried and rehydrated gels to other gel matrices. Fractionating the DNA in ultra-thin matrices results in better signal detection. The matrix subsections of the carrier of the invention have been found to serve the above multiple purposes.

Two matrix carrier designs are described above in detail to illustrate how different types of matrix carriers may be designed to fit the needs of particular DNA-based tests. The following examples are described very briefly to enumerate possible combinations that exist for additional matrix carrier designs.

The automated system as outlined in each of the examples includes sample preparation as the first step and detection (reading and interpreting signal) as the final step. The intermediate steps are defined as those which supply the specificity of nucleic acid sequence to the system and vary among the examples.

EXAMPLE 3

Amplification, Electrophoretic Separation and Hybridization

A variation of Example 2 may be used when electrophoretic band patterns of amplified fragments are ambiguous. Rather than staining all DNA bands for detection as illustrated in Example 2, hybridization with labeled probes permits detection of only those bands having sequence complementarity.

EXAMPLE 4

Amplification, Hybrization and Electrophoretic Separation

A variation of Example 3, in which the order of electrophoresis and hybridization are reversed, may be used when detection of amplification products is improved by electrophoresis after labeled molecular probes have bound to them. The DNA product-labeled probe complex may have a more distinguishable electrophoretic band pattern. Another advantage is that hybridization is more efficient in the smaller volume of a matrix subsection than it is in the volume of a larger matrix section into which DNA has been electrophoresed.

EXAMPLE 5

Hybridization

If in Example 1, sufficient components are present in a specimen, amplification may not be required and the detection would require only hybridization to a labeled probe after sample preparation.

EXAMPLE 6

Hybridization and Electrophoretic Separation

One instance where hybridization followed by electrophoresis would be useful is where labeled DNA probes are hybridized to RNA transcripts and the DNA:RNA hybrids produce a fragment size class distinguishable by electrophoresis. Similarly, labeled DNA or RNA complexes may be cleaved at particular recognition sites and electrophoresed to enhance their detection.

EXAMPLE 7

Hybridization, Electrophoretic Separation and Amplification

If, in Example 6, the amount of target is below detectable levels, amplification increases sensitivity of detection and may be performed after hybridization and electrophoresis.

EXAMPLE 8

Amplification

Amplification that is specific enough for detection without hybridization or electrophoresis is possible. Detection is by measuring the increase in mass of DNA or RNA after amplification. In this case measuring labeled nucleotide incorporation simplifies the assay. Unincorporated, labeled nucleotides may be readily washed away before detection.

Additionally, the more primer sequences used in PCR to amplify more fragments, the more specific is identification of target DNA. There is a dampening effect that limits the number of primer pairs that can be used together, which varies according to the nature of the target and background DNA or RNA. A particular assay may be used in which multiple primer pairs are used to increase the total quantity of DNA in the sample. Duplicate samples are run in parallel on the same matrix as positive and negative controls. The positive controls have primers to amplify a conserved region of specimen DNA that is species-specific and indicates the starting amount of total DNA present in the specimen. Another positive control of known target DNA demonstrates adequate assay conditions. A negative control starts with non-target DNA to indicate possible contamination of assays components.

Specimens that lack primer-binding targets do not increase DNA content and such a test is useful in genetic disease or tumors where deletions of both normal alleles cause a disease state. This test design may also be used to compare the number of copies of a tumorigenic or an oncogenic region with those of a single copy gene in order to quantify the extent to which the gene has been amplified naturally in any given tumor.

EXAMPLE 9

Hybridization and Amplification

The Q-beta replicase method of detection requires hybridization before amplification and may be used in the device of the invention. (Lizardi, P. M., C. E. Guerra, H. Lomeli, I. Tussie-Lune, F. R. Kramer. 1988. Exponential Amplification of Recombinant-RNA Hybridization Probes. *Biotechnol.* 6:1197–1202.) An oligonucleotide probe is inserted in a RNA that serves as a template for RNA synthesis by the enzyme called Q-beta replicase. The enzyme polymerizes multiple RNA transcripts which include the target sequence, generating a relatively large mass of recombinant RNA to indicate that hybridization to the specific oligonucleotide sequence had occurred. Qβ replicase is a RNA-dependent polymerase that replicates a naturally occurring template into which the specific oligonucleotide is inserted and from which recombinant DNA cloned into a plasmid can be use to generate RNA transcripts in vitro with T7 RNA polymerase. The single-stranded, recombinant RNA transcripts are then used as hybridization probes in specimen DNA suspected of containing the specific oligonucleotide. The recombinant RNA probes hybridize specifically to target DNA and retain their ability to be amplified. For amplification, 1.2 μg of Qβ replicase is incubated with the RNA transcripts which had hybridized to the target sequence, in 25 μl of 400 μM each of ATP, CTP, GTP and UTP, one of which is labeled, 14 mM $MgCl_2$, and 90 mM Tris-HCl (ph 7.5) at 37° C. for 25 minutes.

EXAMPLE 10

Hybrization, Amplification and Electrophoretic Separation

Electrophoretic separation after RNA transcripts are produced according to Example 9 is a way to analyze the integrity of the RNA transcripts. The mobility of the RNA provides verification that the relatively large mass of RNA generated is in the size class of desired recombinant RNA.

EXAMPLE 11

Electrophoretic Separation and Hybridization

Restriction Fragment Length Polymorphisms (RFLPs) are DNA fragments resulting from endonuclease cleavage of genomic DNA whose length varies from individual to individual by virtue of whether the specific recognition site of the endonuclease is present or not at a given location in the genome. After electrophoretic separation of these fragments according to size class using the device of the invention, labeled DNA probes are hybridized to these variable regions resulting in unique banding patterns which identify an individual and the individual's relatedness to other individuals. In some instances the same genetic variation that alters the restriction site also causes an abnormal phenotype and thus determines the disease condition directly. In other instances, linkage relationships are established between a genetic defect and an RFLP allele which acts as a genetic marker. RFLP's are used to identify genetic diseases or predict chances that offspring will inherit a genetic disease. They may also be used to prove or disprove identity in paternity or forensic cases.

EXAMPLE 12

Electrophoretic Separation

Electrophoretic separation in the device without amplification or hybridization may be sufficient to provide useful information. In less genetically complex organisms the electrophoretic banding pattern of endonuclease-restricted total genomic DNA yields strain or species identity. In bacteria, for example, a densitometric scan of these electrophoretic bands can distinguish one kind of bacteria from another.

EXAMPLE 13

Electrophoretic Separation and Amplification

Amplification of a specific size class of the restricted DNA may be performed directly in the same hydrogel matrix in which the size classes have been separated in the device. In cases where more than species identification is necessary, electrophoresis first helps purify DNA from the total specimen. Then amplification before final DNA detection means that specificity of amplification is combined with specific electrophoretic mobility to make detection of signal stronger and thereby easier over background DNA.

EXAMPLE 14

Electrophoretic Separation, Amplification, and Hybridization

Hybridizing a labeled nucleic acid probe to nucleic acid targets produced as according to Example 13 is a way to determine the presence of specific DNA targets, thus reducing matrix background signal and simplifying software interpretation of the results.

EXAMPLE 15

Electrophoretic Separation Hybrization, and Amplification

Initial electrophoresis of nucleic acids as in Examples 11–14 may be followed by hybridization with one or more primary molecular probes, which are then amplified by one of the transcription-based methods such as the Q Beta replicase method (see Lizardi et al., cited in Example 9).

While the invention has been described in detail with respect to specific illustrative examples and embodiments, it will be apparent that numerous other variations, modifications, and embodiments are possible, and accordingly all such variations, modifications and embodiments are to be regarded as being within the spirit and scope of the invention. Such variations include, but are not limited to the detection of RNA or protein or other cellular components in the device using known detection methods and reagents.

The ability to monitor specific nucleic acid sequences in biological material allows surveillance of genetic changes and fate-monitoring of known genetic changes. Both the lack of sensitivity of current probes and the labor-intensive preparation of the biological material has slowed application of recombinant DNA technology. The sensitivity of gene probes is increasing but some biological samples, especially those from the environment or a large population base, require massive sampling and screening to monitor the dispersal of the target gene. This method, which eliminates tedious sample preparation by automating the procedure, expands the ability to study gene competition, stability, dispersion and evaluate efficacy of new, recombinant DNA product treatments.

What is claimed is:

1. A process for handling a single specimen for the analysis of nucleic acid sequences, comprising:
    (a) immobilizing said specimen in a device comprising a top cover portion and a bottom housing portion, said top cover portion hingedly moved to a closed position; said bottom housing portion having an extended area on a first side of said bottom housing portion extending beyond said top cover portion; wherein said bottom housing portion has edges defining a space, said space comprises a fluid receiving area in the extended area and a thin, flat matrix and specimen holding area; said fluid receiving area being in fluid communication with said matrix and specimen holding area; wherein immobilizing the specimen in the matrix and specimen holding area is by means selected from the group consisting of standard fixatives and gel matrix materials; which matrix and specimen holding area is defined by the top cover portion when said top cover portion is in a closed position;

(b) adding a first treatment fluid to said fluid receiving area wherein the first treatment fluid fills said matrix and specimen holding area forming a liquid film in contact with the top cover portion and the matrix and specimen, said treatment fluids selected from the group consisting of lysing and denaturing solutions, wash and rinse solutions, amplification, hybridization and detection reagents and electrophoresis buffers; wherein said treatment fluids are added to the device so that the nucleic acids of the immobilized specimen are treated in place on the device; wherein the top cover portion is in said closed position during amplification;

(c) controlling the temperature of the carrier device for incubating a treatment fluid with the specimen at a desired temperature for a desired time period, said temperature control selected from the group consisting of maintaining and changing the temperature of the device;

(d) adding a volume of a second treatment fluid equal to the volume of the first treatment fluid wherein the first fluid volume exits the matrix and specimen holding area opposite where the fluids are added;

(e) repeating the addition of fluids sufficient to rinse away the prior treatment fluid and bring the next treatment fluid into contact with the specimen in the matrix and specimen holding area;

wherein the detection reagents are used to visualize and enumerate individual locations of the nucleic acids in place within the specimen.

2. A process for specimen handling according to claim 1, wherein step a) comprises mixing the matrix material in a liquid state with the specimen; wherein the matrix material fills the matrix and specimen holding area with the top cover portion in the closed position and then the matrix material gels embedding the specimen therein; wherein said gel matrix is dehydrated by heating said device with the device in the open position in such a way that the matrix shrinks to an ultra-thin layer; wherein said dehydrated gel matrix is rehydrated after dehydration.

3. A process for specimen handling according to claim 1; wherein the matrix and specimen holding area of said device is divided into sections such that at least one of the sections contains a gel matrix material; wherein applying current through wires making electrical contact directly with the gel formed in the matrix and specimen holding area and indirectly through fluids in the fluid receiving area; wherein the electrophoretic transfer of macromolecules from one matrix section to another occurs.

4. A process for specimen handling according to claim 1; wherein the specimen is suspected of containing at least one specific nucleic acid sequence; wherein the incubations are repeated with treatment fluids appropriate to enzymatically amplify a specific nuclear acid sequence within the specimen sufficient for detection of the specific nuclear acid sequence; and wherein the enzymes used are selected from the group consisting of polymerases and ligases.

5. A process for specimen handling for the analysis of according to claim 1; wherein said detection reagents are selected and include probes containing labels selected from the group consisting of fluorescent, chromogenic and luminescent labels; said process further comprising microscopically observing the specimen through an optically clear portion of said device.

* * * * *